United States Patent
Lin et al.

(10) Patent No.: US 9,861,673 B2
(45) Date of Patent: Jan. 9, 2018

(54) EXTRACT FROM INDIGO NATURALIS AND A PROCESS FOR PREPARING THE SAME

(71) Applicant: Galderma S.A., Cham (CH)

(72) Inventors: Yin-Ku Lin, Keelung (TW); Isabelle Cardinaud, Antibes Juan les Pins (FR); Philippe Andres, Peymeinade (FR); Laurent Chantalat, Antibes (FR); Jean-Thomas Pierson, Avignon (FR); Antoine Bily, Vedene (FR); Loïc Le Bronec, Morieres les Avignon (FR)

(73) Assignee: Galderma S.A., Cham (CH)

( * ) Notice: Subject to any disclaimer, the term of this patent is extended or adjusted under 35 U.S.C. 154(b) by 0 days.

(21) Appl. No.: 15/592,893

(22) Filed: May 11, 2017

(65) Prior Publication Data

US 2017/0266248 A1    Sep. 21, 2017

Related U.S. Application Data (63) Continuation of application No. PCT/EP2016/057761, filed on Apr. 8, 2016.

(30) Foreign Application Priority Data

Apr. 9, 2015    (EP) .................................... 15163060

(51) Int. Cl.
| | | |
|---|---|---|
| *A61K 36/00* | (2006.01) | |
| *A61K 36/70* | (2006.01) | |
| *A61K 36/48* | (2006.01) | |
| *A61K 36/315* | (2006.01) | |
| *A61K 36/19* | (2006.01) | |
| *A61K 31/404* | (2006.01) | |

(52) U.S. Cl.
CPC ............ *A61K 36/70* (2013.01); *A61K 31/404* (2013.01); *A61K 36/19* (2013.01); *A61K 36/315* (2013.01); *A61K 36/48* (2013.01); *A61K 2236/31* (2013.01); *A61K 2236/33* (2013.01); *A61K 2236/51* (2013.01); *A61K 2236/53* (2013.01)

(58) Field of Classification Search
CPC .................................................... A61K 36/00
See application file for complete search history.

(56) References Cited

U.S. PATENT DOCUMENTS

| | | |
|---|---|---|
| 2010/0034757 A1 | 2/2010 | Fujii et al. |
| 2012/0213868 A1 | 8/2012 | Lin |
| 2013/0331400 A1 | 12/2013 | Kusakari et al. |
| 2014/0243354 A1 | 8/2014 | Chantalat et al. |

FOREIGN PATENT DOCUMENTS

| | | | |
|---|---|---|---|
| CN | 1317322 A | | 10/2001 |
| EP | 0987027 A1 | | 3/2000 |
| EP | 1495762 A1 | | 1/2005 |
| EP | 1495764 A1 | | 1/2005 |
| EP | 2489358 A1 | | 8/2012 |
| JP | 2006-241080 A | | 9/2006 |
| KR | 2005077310 A | * | 8/2005 |
| KR | 2013071857 A | * | 7/2013 |
| WO | 2014118040 A1 | | 8/2014 |

OTHER PUBLICATIONS

Chiang, An in vitro study of the antimicrobial effects of indigo naturalis prepared from Strobilanthes formosanus Moore. Molecules (Basel, Switzerland), (Nov. 21, 2013) vol. 18, No. 11, pp. 14381-14396.*
Int'l Search Report and Written Opinion dated Jun. 20, 2016 in Int'l Application No. PCT/EP2016/057761.
Int'l Search Report and Written Opinion dated Jun. 20, 2016 in Int'l Application No. PCT/EP2016/057763.
Int'l Search Report and Written Opinion dated Jun. 21, 2016 in Int'l Application No. PCT/EP2016/057769.
Han et al, "Genuine traditional Korean medicine, Naju Jjok (Chung-Dae Polygonum tinctorium) improves 2,4-dinitrofluorobenzene-induced atopic dermatitis-like lesional skin," Phytomedicine, vol. 24, pp. 453-460 (2014).
Han et al, "Tryptanthrin ameliorates atopic dermatitis through down-regulation of TSLP," Archives of Biochemistry and Biophysics, vol. 542, pp. 14-20 (2013).

* cited by examiner

*Primary Examiner* — Qiuwen Mi
(74) *Attorney, Agent, or Firm* — Panitch Schwarze Belisario & Nadel LLP (57) ABSTRACT

The present invention relates to a process for preparing an extract from one or more botanical raw materials, such as Indigo Naturalis and the extract itself. The present invention also relates to a composition comprising the extract, as well as the use of composition in medical or cosmetic applications.

12 Claims, 6 Drawing Sheets

EXTRACT FROM INDIGO NATURALIS AND A PROCESS FOR PREPARING THE SAME

CROSS-REFERENCE TO RELATED APPLICATION

This application claims the benefit, under 35 U.S.C. §365 of International Application PCT/EP2016/057761 filed Apr. 8, 2016, which was published in the English language on Oct. 13, 2016, under International Publication No. WO/2016/162484 A1, and which claims the benefit of European patent application No. 15163060.5, filed Apr. 9, 2015, the disclosure of each of which is hereby incorporated by reference herein in its entirety.

TECHNICAL FIELD

The present invention relates to a process for preparing an extract from one or more botanical raw materials, such as Indigo Naturalis and the extract itself. The present invention also relates to a composition comprising the extract, as well as the use of composition in medical or cosmetic applications.

BACKGROUND

The conventional treatments for psoriasis are generally designed according to the age, gender, occupation and cognitive ability of a patient, the types and distribution of lesions, patient's response(s) to previous therapeutic method(s), and other medical histories of the patient. The primary therapeutic methods for psoriasis include topical therapy, systemic therapy, injection of biologics and phototherapy. Compositions for topical therapy include, e.g., corticosteroids, anthralin (available as Margiton®), coal tar (available as Polytar®), calcitriol (available as Silkis®), tazarotene (available as Tazorac®), salicylic acid, and these compositions are suitable for treating psoriasis patients with mild symptoms. Oral preparations of e.g., methotrexate (MTX), cyclosporine, and retinoids are commonly used for systemic therapy and are suitable for treating psoriasis patients with medium to severe symptoms. Biologics include alefacept (available as Amevive®), efalizumab (available as Raptiva®), etanercept (available as Enbrel®) and adalimumab (available as Humira®), and they are suited for injecting into psoriasis patients with medium to severe symptoms. Phototherapy, e.g., ultraviolet B (UVB) phototherapy, photochemotherapy such as psoralen plus ultraviolet A (PUVA), is suitable for treating psoriasis patients with severe symptoms.

However, additional therapeutic methods are desirable.

SUMMARY

Indigo Naturalis, for example Qingdai, is a dark-blue powder prepared from leaves of Indigo-bearing plants or Indigo-producing plants. Said plants are preferably selected from the group consisting of *Indigofera tinctoria* L., *Baphicacanthus cusia* (Nees) Bremek (syn. *Strobilanthes cusia* (Nees), *Persicaria tinctoria* (Aiton) Spach. (syn. *Polygonum tinctorium* Aiton, *P. tinctorium* Lour.) and *Isatis tinctoria* L. (syn. *Isatis indigotica* Fort.).

One of the drawbacks encountered with the use of Indigo Naturalis or Qingdai is the dark color it produces on the skin and it leaves stains on clothes. Qingdai is the current name for Indigo Naturalis, it is extracted from Indigo-bearing or Indigo-producing plants with a NaOH or KOH aqueous solution and corresponds to a mixture of around 5-15% organic compounds including alkaloids among which indigo and indirubin are present, and 85-95% inorganic compounds such as calcium carbonate and calcium hydroxide.

Another drawback may be that traditionally, only indigo and indirubin are controlled in Indigo Naturalis product.

Thus, there remains an unmet need to develop an extract from Indigo Naturalis or from Indigo-bearing or Indigo-producing plants into a marketable drug, to obtain an extract less colored than Indigo Naturalis and to characterize and control the majority of the components of such extract. More specifically, it would be advantageous to provide an extract less colored while maintaining or increasing its efficacy for treatment or alleviation of skin diseases or disorders such as psoriasis.

The present invention solves this problem by providing with an easy-to-handle refined extract retaining active components from Indigo Naturalis or Qingdai to ensure clinical efficacy and safety.

The present invention, in part, deals with a process for obtaining an extract from Indigo Naturalis, for example from Qingdai, that in turn contains e.g., indirubin and indigo for treatment or alleviation of skin diseases or disorders such as psoriasis.

In one aspect, the present invention provides a process for preparing an extract from one or more botanical raw materials, such as Indigo Naturalis or the leaves and/or stems of one or more Indigo-bearing plants or indigo-producing plants, preferably selected from the group consisting of *Indigofera tinctoria* L., *Baphicacanthus cusia* (Nees) Bremek (syn. *Strobilanthes cusia* (Nees), *Persicaria tinctoria* (Aiton) Spach. (syn. *Polygonum tinctorium* Aiton, *P. tinctorium* Lour.) and *Isatis tinctoria* L. (syn. *Isatis indigotica* Fort.). The process comprises the following steps:

a) an extraction step: extracting Indigo Naturalis or the leaves and/or stems of one or more plants as selected above with a first polar solvent or moderately polar solvent to obtain a mixture of extraction;

b) a filtration step: filtering the mixture of extraction to obtain a filtrate;

c) a concentration step: concentrating the filtrate to obtain a crude extract;

d) a washing step: washing the crude extract with a non-polar solvent, and optionally a second polar solvent, to obtain a washing mixture; and e) a filtration step: filtering the washing mixture to obtain a refined extract optionally after a drying step, for example, according to a conventional method for drying.

The process according to the invention allows obtaining a refined extract; such a refined extract is as defined below. In the following description, the term "botanical raw material" refers to Indigo Naturalis (for example, commercially available Qingdai), or leaves and/or stems of an Indigo-bearing plant or Indigo-producing plant, preferably selected from the group consisting of *Indigofera tinctoria* L., *Baphicacanthus cusia* (Nees) Bremek (syn. *Strobilanthes cusia* (Nees), *Persicaria tinctoria* (Aiton) Spach. (syn. *Polygonum tinctorium* Aiton, *P. tinctorium* Lour.) and *Isatis tinctoria* L. (syn. *Isatis indigotica* Fort), after harvest and collection, may be processed by, for example, fermentation.

In some embodiments, the solvent used in the extraction step a) may include, but is not limited to, dimethyl formamide (DMF), ethyl acetate, ethanol (including aqueous ethanol such as, for example, 85% ethanol), dimethylsulfoxide (DMSO), dichloromethane (DCM), tetrahydrofuran (THF), dimethylacetamide (DMA), acetone, 2-butanone, acetonitrile, isopropyl acetate, 2-methyl tetrahydrofurane (MeTHF), methyl tert-butyl ether, water, methanol, chloroform, terpene (limonene, p-cimene, etc.), or a combination thereof. Preferably, the solvent can be ethyl acetate, MeTHF, ethanol or aqueous ethanol.

Further, the extraction step a) can be conducted at a ratio of botanical raw material to solvent (i.e., the gram of the material to be extracted to the mL of the solvent) in a range from 1:5 to 1:150 (g/mL), for example, in a range from 1:5 to 1:100, for example, 1:6, 1:15, 1:20, 1:30, 1:50, 1:100.

In a particular embodiment, the solvent used in the extraction step a) is an organic solvent. More preferably, the solvent is selected from the group consisting of dimethylformamide, ethyl acetate, ethanol, dimethylsulfoxide, dichloromethane, tetrahydrofuran, dimethylacetamide, acetone, 2-butanone, acetonitrile, isopropyl acetate, 2-methyl tetrahydrofuran, methyl tert-butyl ether, methanol, chloroform, terpene and a combination thereof.

In some embodiments, the extraction step a) can be repeated until there is less than 0.10% of indirubin content (% w/w) in the remaining botanical raw material filtered at the filtration step b) as measured by the HPLC method disclosed in Example 8A.

In some other embodiments, the extraction step a) is performed by heating, for example till reflux.

The extraction step a) is followed by a filtration step b), and then a concentration step c) for concentrating the filtrate to provide a crude extract. The filtration step b) can be performed while hot.

In some embodiments, the washing step d) can be repeated until the amount of indirubin (% w/w) in the refined extract is at least 55% (w/w) as measured by the HPLC method disclosed in Example 8A.

In some embodiments, the solvent used in washing step d) is selected from the group comprising water, an alkane with 5 to 8 carbon atoms, an alcohol with 2 to 6 carbon atoms and a combination thereof. For example, the solvent includes, but is not limited to, hexane, heptane, ethanol, water or a combination thereof. For example, in the washing step d), hexane or heptane, and aqueous ethanol are used in sequence or simultaneously in the case that two or more of the solvents are used.

According to an embodiment, the non-polar solvent used in step d) is hexane.

According to another specific embodiment, step d) is carried out with a non-polar solvent and a second polar solvent. Preferably, the second polar solvent is ethanol. More preferably, the non-polar solvent used in step d) is hexane and the second polar solvent is ethanol.

In some other embodiments, a crude extract obtained from the concentration step c) is subjected to the following procedure for at least one cycle till obtaining a refined extract: the crude extract is washed by a solvent (step d)), and filtered (step (e)) to yield a refined extract, optionally followed by a drying step. According to a specific embodiment, the washing step d) and filtration step e) are performed by only one cycle to obtain the refined extract. When more than one cycle is applied, the same or different solvents for washing can be used. Further, the crude extract can be washed with a solvent under reflux, the mixture can be cooled to room temperature and then filtered to yield a refined extract, optionally followed by a drying step.

In a preferred embodiment, two cycles are performed. Particularly, the crude extract obtained by the concentration step c) is washed in a non-polar solvent, preferably hexane (step d) and filtered (step e), optionally followed by a drying step. The hexane extract is then washed by an organic polar solvent, preferably ethanol (step d) and then filtered (step e) to obtain a refined extract, optionally followed by a drying step.

Optionally, a micronization step is performed after step e), providing thereby a refined extract having a particle size between 25 and 35 μm, preferably of about 30 μm.

In another preferred embodiment, when the refined extract is micronized in the last step, 99% of the obtained particles are less or equal to 30 μm.

In another aspect, the present invention provides a refined extract from Indigo Naturalis.

The present invention also provides a refined extract containing indirubin as a component in an amount of at least 55% (w/w) of the refined extract. In some embodiments, indirubin is present in an amount of at least 60%, 65%, 70%, 75%, 80% or 85% (w/w) of the refined extract. For example, the indirubin can be in an amount of 55-90% (w/w) of the refined extract, e.g., 55-60%, 55-65%, 55-70%, 55-75%, 55-80%, 55-85%, 55-90%, 60-65%, 60-70%, 60-75%, 60-80%, 60-85%, 60-90%, 65-70%, 65-75%, 65-80%, 65-85%, 65-90%, 70-75%, 70-80%, 70-85%, 70-90%, 75-80%, 75-85%, 75-90%, 80-85%, 80-90%, or 85-90% (w/w) of the refined extract.

Preferably, the present invention provides a refined extract containing indirubin as a component in an amount of at least 65% (w/w) of the refined extract.

Preferably, the indirubin is in an amount of 65-90% (w/w) of the refined extract.

In some embodiments, the refined extract contains indigo as a component. Indigo can be in an amount of 0-15% (w/w) of the refined extract, for example, 0.1-15%, 0.5-15%, 1-15%, 2-15%, or 3-15% (w/w) of the refined extract.

In some other embodiments, the refined extract further contains tryptanthrin as a component. Tryptanthrin can be in an amount of 0.01-5% or preferably 0.1-5% (w/w) of the refined extract, for example, 0.01-1%, 0.05-1%, 0.1-1%, 0.1-5%, 0.5-1%, or 0.5-5% (w/w) of the refined extract.

In further some embodiments, the refined extract further contains qingdainone as a component. Qingdainone can be in an amount of 0.1-5% (w/w) of the refined extract, for example, 0.1-1%, 0.1-5%, 0.5-1%, or 0.5-5% (w/w) of the refined extract.

In further some other embodiments, in the refined extract, comprising two or more of those described above, represents at least 60% (w/w) of the refined extract, for example 65%, 70%, 75%, 80%, 85%, 90%, or 95% (w/w), and preferably at least 90% (w/w). The characterized components, comprising two or more of those described above, are in an amount of 60-99% (w/w) of the refined extract, for example 60-95%, 65-95%, 70-95%, 80-95%, 85-95%, 90-95%, 60-99%, 65-99%, 70-99%, 80-99%, 85-99% or 90-99% (w/w) and preferably in an amount of 90-99% (w/w).

In further another aspect, the present invention provides a pharmaceutical composition comprising a refined extract as described above, and a pharmaceutically acceptable carrier. The composition is in the form for topical or oral administration.

In further another aspect, the present invention provides a cosmetic composition comprising a refined extract as described above, and a cosmetically acceptable carrier. The composition is in the form for topical administration.

In still another aspect, the present invention provides a use of the refined extract in the preparation of a pharmaceutical or cosmetic composition for inhibiting proliferation or differentiation of keratinocytes, inhibiting infiltration of mononuclear cells into the dermis and epidermis, inhibiting vascular alteration resulting in hyperplastic blood vessels, or inhibiting up-regulation of adhesion molecules on endothelia cells. The use comprises administering the just-described composition to a subject (e.g. human) in need thereof.

In further another aspect, the present invention provides an afore-described composition for the treatment or alleviation of a skin disease or condition selected from the group consisting of psoriasis, inflammatory skin conditions, onychomycosis, skin cancer, abnormal keratinization induced diseases, skin aging, pustulardermatosis and Cutaneous T Cell Lymphoma (CTCL).

In another aspect, the present invention provides a method for inhibiting proliferation or differentiation of keratinocytes, inhibiting infiltration of mononuclear cells into the dermis and epidermis, inhibiting vascular alteration resulting in hyperplastic blood vessels, or inhibiting up-regulation of adhesion molecules on endothelia cells, which comprises a step of contacting the refined extract of the present invention to a cell in need thereof. This method may be applied in vitro or in vivo.

In still further another aspect, the present invention provides a method for the treatment of skin disease or condition comprising administering an effective amount of the refined extract according to the present invention to subjects in need thereof. The disease or condition is selected from the group consisting of psoriasis, inflammatory skin conditions, onychomycosis, skin cancer, abnormal keratinization induced diseases, skin aging, pustulardermatosis and CTCL.

In some embodiments, the inflammatory skin conditions can be atopic dermatitis, eczema or superinfected skin. The skin aging can be skin rejuvenation, tissue regeneration for scars or skin senescence. The abnormal keratinization can be acne, ichtyosis or palmoplantar keratoderma. The skin cancer can be precancerous skin cancer, for example, Actinic Keratosis (AK), Bowen's disease; skin cancer, for example, SCC, BCC, NMSC; melanoma and HPV induced skin cancer.

DESCRIPTION OF DRAWINGS

The above and other features and advantages of the present invention will become apparent with reference to the following detailed description and the accompanying drawings.

FIG. 1: Illustrative HPLC chromatograms of indigo (A) and indirubin (B).

FIG. 2: Illustrative HPLC chromatograms of thryptanthrin (A), Qingdai (B) and a refined extract of Example 2 (C).

DETAILED DESCRIPTION

As used herein, indirubin, indigo, tryptanthrin, and qingdainone have the formulas as mentioned in the literature, and more particularly the following structures.

Indirubin

Indigo

Tryptanthrin or

Qingdainone

A "polar solvent" refers to a solvent having a high dielectric constant and a high dipole moment; and examples include water, alcohols, for example, alcohols from 2 to 6 carbon atoms (such as ethanol), acetonitrile, dimethylfomamide (DMF), and dimethylsulfoxide (DMSO).

A "moderately polar solvent" refers to a solvent having moderately high dielectric constant; and examples include ethyl acetate, dichloromethane (DCM), tetrahydrofuran (THF), dimethylacetamide (DMA), acetone, 2-butanone, isopropyl acetate, 1,4-dioxane, 2-methyltetrahydrofuran (MeTHF), methyl tert-butyl ether (MTBE).

A "non-polar solvent" refers to a solvent having low dielectric constant; and examples include diethyl ether, petroleum ether (PE), toluene and alkanes from 5 to 8 carbon atoms, for example, heptane, hexane, pentane or cyclohexane.

A "room temperature" refers to 18° C.-35° C.

The term "psoriasis" or "psoriasis disease" refers to all types of psoriasis well known to those skilled in the art. It includes, but is not limited to, chronic plaque psoriasis, guttate psoriasis, erythrodermic psoriasis, pustular psoriasis, inverse psoriasis (also known as flexural psoriasis), nail psoriasis, psoriatic arthritis.

The term "refined extract" refers to a solid, semi-solid or oily extract, preferably solid extract, which contains less than 10% (w/w) of water and/or solvents used in the process for preparing the said refined extract. A refined extract is more preferably characterized by an increase amount of active ingredients, including alkaloids among which indigo, indirubin, tryptanthrin, and/or qingdainone are present, preferably enriched in indirubin, compared to Qingdai or Indigo Naturalis. More specifically, the refined extract according to the invention comprises at least 60%, or more preferably more than 70%, (w/w) of active ingredients, including indigo, indirubin, tryptanthrin, and/or qingdainone.

The term "crude extract", as used herein, refers to a solid, semi-solid or oily extract, preferably solid or semi-solid extract, which contains less than 15% (w/w) (e.g., 5-15%, 5-10%) of water and/or solvents used in the process for preparing the refined extract. The crude extract is less enriched in indirubin, than the refined extract as compared to Qingdai or Indigo Naturalis. The crude extract is obtained by the concentration step c) according to the invention. The concentration step is more particularly carried out by sending the filtrate to a concentrator (for instance at reduced pressure), as to remove water and/or solvents used in the process and concentrating thereby the active ingredients present in the extract, including indigo, indirubin, tryptanthrin, and/or qingdainone.

"one cycle", as used herein, refers to the two steps of the washing step d) and filtration step e) which are performed sequentially once. "two cycles", as used herein, refers to the two steps of the washing step d) and filtration step e) which are performed sequentially twice.

The term "an effective amount" refers to a dose level of the refined extract which yields a therapeutic benefit (for example, amelioration, alleviation or cure of the diseases, disorders or symptoms) to a patient on average.

The present invention provides a process for preparing a refined extract from Indigo Naturalis or from the leaves and/or stems of one or more Indigo-bearing plants or Indigo-producing plants, preferably selected from the group consisting of *Indigofera tinctoria* L., *Baphicacanthus cusia* (Nees) Bremek (syn. *Strobilanthes cusia* (Nees), *Persicaria tinctoria* (Aiton) Spach. (syn. *Polygonum tinctorium* Aiton, *P. tinctorium* Lour.) and *Isatis tinctoria* L. (syn. *Isatis indigotica* Fort.).

Indigo Naturalis is obtained from leaves and stems, preferably from leaves, of *Indigofera tinctoria* L., *Baphicacanthus cusia* (Nees) Bremek (syn. *Strobilanthes cusia* (Nees), *Persicaria tinctoria* (Aiton) Spach. (syn. *Polygonum tinctorium* Aiton, *P. tinctorium* Lour) and *Isatis tinctoria* L. (syn. *Isatis indigotica* Fort.). Preferably, Indigo Naturalis is obtained from leaves and stems of *Persicaria Tinctoria* and/or *Baphicacanthus cusia*.

While Indigo Naturalis is commercially available (examples of Indigo Naturalis commercially available (plant/supplier): *Baphicacanthus cusia*/Delong; *Indigofera tinctoria*/KMA exports or Sam Vegetable Colours PVT Ltd; *Isatis tinctoria*/Andrea Primavera or Bleu de Lectoure; *Polygonum tinctorium*/CouleurGarance or EARL 4 saisons), it can be produced from the leaves and stems of one or more of above plants by methods commonly known in the art. These methods can be summarized as follows: freshly harvested stems and leaves of *Persicaria Tinctoria* and/or *Baphicacanthus cusia* are added to a pool in the open air, the water is added to the pool to cover the stems/leaves. After soaking for few days (26-30° C.), the stems/leaves will become rotten. Then lime soda is added while stirring. When the color of the soaking mixture changed from green to deep violet, the precipitate is collected, washed (usually with water for 2-3 times), and then dried to yield Indigo Naturalis powder.

A refined extract may be prepared by a process according to the invention comprising the following steps consisting of: a) (i) adding an extracting solvent, a polar or moderately polar solvent (such as an alcohol or ethyl acetate), to Indigo Naturalis powder to yield a mixture; (ii) heating and stirring the mixture for a period of time (e.g., 30 min, 1 hour, 2 hours); b) (iii) filtering the heated mixture while hot to remove insoluble by-products to yield a filtrate; c) (iv) concentrating the filtrate to yield a crude extract; d) (v) adding a washing solvent (for example, water, or a non-polar, or a polar solvent or a mixture thereof) to the crude extract to yield a washing mixture; (vi) heating and stirring the washing mixture for a period of time (e.g., 30 min, 1 hour, 2 hours); e) (vii) filtering the washing mixture, for example at room temperature (e.g. 18° C.-35° C.) to collect a refined extract; optionally (viii) repeating steps (v) to (vii) until the amount of indirubin (% w/w) in the residue (i.e., the extract) is more than 55% (w/w), preferably more than 65% (w/w), as measured by HPLC method disclosed in Example 8A, optionally (ix) drying the refined extract according to a conventional method (e.g., air-drying, lyophilization). The washing solvent in steps (v) and (viii) can be the same or different.

In a preferred embodiment, a refined extract is prepared by a process comprising the steps of:
 a) extracting Indigo Naturalis with ethanol at reflux between 2 and 8 hours,
 b) filtering the mixture at a temperature not less than 65° C. to obtain a filtrate,
 c) concentrating the filtrate, to obtain a crude extract, said crude extract is optionally filtered (with addition of water) in order to remove completely the solvent and the last components still present in the solvent and dried,
 d) (i) washing the crude extract with hexane at a temperature not less than 50° C. between 15 and 60 min,
  (ii) filtering at room temperature the mixture obtained at step d) (i) to obtain a product, optionally rinsing it with ethanol and water
  (iii) washing the product obtained at step d) (ii) with ethanol at reflux, and
 e) filtering at room temperature the washing mixture obtained at step d) and drying the resulting product at a temperature less than 80° C. to obtain an extract which is optionally micronized.

In another preferred embodiment, when the refined extract is micronized in the last step, the particle size is around 99% in the range 25 to 35 μm, preferably of about 30 μm.

As used herein, "about" or "around" will be understood by a person of ordinary skill in the art and will vary to some extent on the context in which it is used. If there are uses of the term which are not clear to persons of ordinary skill in the art given the context in which it is used, "about" or "around" will mean up to plus or minus 20%, preferably 10% of the particular term.

The contents of ingredients such as indigo, indirubin, tryptanthrin and qingdainone can be quantitated by HPLC methods as disclosed in Example 8.

The just described process makes it possible to obtain a refined extract that is easy to handle and can be further formulated in pharmaceutical or cosmetic compositions. Moreover, the process provides an extract with an enriched indirubin. At least 60% (w/w) of the component of the refined extract thus obtained are characterized; preferably at least 90% (w/w), among them one or more are selected from the list consisting of indigo, indirubin, tryptanthrin and qingdainone. While the refined extract obtained from the process is in a solid form, a preparation of a liquid form for the refined extract may be made based on handling or formulating needs by a simple dissolution or solubilization of the solid refined extract.

In this case, a liquid form for the refined extract may be prepared by a process according to the invention comprising the following steps consisting of: a) (i) adding an extracting solvent, a polar or moderately polar solvent (such as an alcohol or ethyl acetate), to Indigo Naturalis powder to yield a mixture; (ii) heating and stirring the mixture for a period of time (e.g., 30 min, 1 hour, 2 hours); b) (iii) filtering the heated mixture while hot to remove insoluble by-products to yield a filtrate; c) (iv) concentrating the filtrate to yield a crude extract; d) (v) adding a washing solvent (for example, water, or a non-polar, or a polar solvent, or a mixture thereof) to the crude extract to yield a washing mixture; (vi) heating and stirring the washing mixture for a period of time (e.g., 30 min, 1 hour, 2 hours); e) (vii) filtering the washing mixture, for example at room temperature (e.g. 18° C.-35° C.), to collect a refined extract; optionally (viii) repeating steps (v) to (vii) until the amount of indirubin (% w/w) in the residue (i.e., the extract) is more than 55% (w/w), preferably more than 65% (w/w), as measured by HPLC method disclosed in Example 8A, (ix) solubilizing the refined extract thus obtained in a pharmaceutically acceptable solvent or carrier. The washing solvents in steps (v) and (viii) can be the same or different.

The present invention also provides an extract obtainable by the process as described above, preferably from a plant extract, an Indigo Naturalis extract or an extract from the leaves and/or stems of an Indigo-bearing plant or Indigo-producing plant, preferably selected from the group consisting of *Indigofera tinctoria* L., *Baphicacanthus cusia* (Nees) Bremek (syn. *Strobilanthes cusia* (Nees), *Persicaria tinctoria* (Aiton) Spach. (syn. *Polygonum tinctorium* Aiton, *P. tinctorium* Lour.) and *Isatis tinctoria* L. (syn. *Isatis indigotica* Fort.), said obtainable extract includes indirubin as a component in an amount of at least 55% (w/w) of the refined extract, preferably at least 65% (w/w). The refined extract is in a solid form and may be prepared by the process described above or any other suitable process. The refined extract may further include indigo, tryptanthrin, and/or qingdainone, which may be co-extracted together with indirubin. In particular, the extract containing multi-ingredients may provide a synergistic effect.

The present invention further provides a pharmaceutical composition comprising the refined extract. The pharmaceutical composition may be formulated into a suitable dosage form for topical or oral administration using technology well known to those skilled in the art. The pharmaceutical composition can additionally comprise a pharmaceutically acceptable carrier such as those widely employed in the art of drug-manufacturing. For instance, the pharmaceutically acceptable carrier may include one or more of the following agents: solvents, emulsifiers, suspending agents, decomposers, binding agents, excipients, stabilizing agents, chelating agents, diluents, gelling agents, preservatives, lubricants, absorption delaying agents, liposomes, and the like. Preferably, solvents are selected from the group consisting of water, glycerol, ethanol, propylene glycol, butylene glycol, dipropylene glycol, ethoxylated or propoxylateddiglycols, cyclic polyols, petroleum jelly, a vegetable oil and any mixture of these solvents. Preferably, the pharmaceutical composition is formulated into a topical formulation that can be directly applied to the skin, for example, a skin suffering from psoriasis. The topical formulation suitable for the pharmaceutical composition may be an emulsion, a gel, an ointment, a cream, a patch, an embrocation, an aerosol, a spray, a lotion, a serum, a paste, a foam, or a drop. In one embodiment of the present invention, the pharmaceutical composition is formulated into an external preparation by admixing the refined extract according to the present invention with a base such as those that are well known and commonly used in the art.

In some embodiments, the dosage and the frequency of administration of the pharmaceutical composition according to the present invention may vary depending on the following factors: the severity of the disease to be treated, the route of administration, and the weight, age, physical condition and response of the subject to be treated. In further or additional embodiments, the amount of the refined extract is in the range of about 0.001 to about 1000 mg/kg body weight/day, for example, about 0.01 to about 500, 300, or 100 mg/kg body weight/day.

The present invention also provides a cosmetic composition comprising the refined extract. The cosmetic composition may be present in a form adapted for topical application comprising a cosmetically or dermatologically acceptable carrier or medium. "Cosmetically or dermatologically acceptable" means media which are suitable for a use in which they come into contact with the skin or human skin appendages without posing a risk of toxicity, intolerance, instability, allergic reaction, etc. In the cosmetic composition, the refined extract may be previously solubilized in one or more cosmetically or dermatologically acceptable solvents, such as water, glycerol, ethanol, propylene glycol, butylene glycol, dipropylene glycol, ethoxylated or propoxylateddiglycols, cyclic polyols, petroleum jelly, a vegetable oil or any mixture of these solvents.

The refined extract and compositions above can be used in the treatment or alleviation of a disease or condition. By treatment it is meant at least an alleviation of the symptoms associated with the pathological condition afflicting the subject, where alleviation is used in a broad sense to refer to at least a reduction in the magnitude of a parameter, e.g. symptom, associated with the pathological condition being treated, such as dermatitis, psoriasis and the like. As such, treatment also includes situations where the pathological condition, or at least symptoms associated therewith, are completely inhibited, e.g., prevented from happening, or stopped, e.g., terminated, such that the host no longer suffers from the pathological condition, or at least the symptoms that characterize the pathological condition. As such, treatment includes both curing and managing a disease condition. Accordingly, the extract and compositions above can be used in the treatment or alleviation of a disease or condition selected from the group consisting of psoriasis, inflammatory skin conditions, onychomycosis, skin cancer, abnormal keratinization induced diseases, skin aging, and pustulardermatosis.

The present invention further provides a method for inhibiting proliferation or differentiation of keratinocytes, inhibiting infiltration of mononuclear cells into the dermis and epidermis, inhibiting vascular alteration resulting in hyperplastic blood vessels, or inhibiting upregulation of adhesion molecules on endothelia cells comprising administering the extract and compositions above to a subject in need thereof.

The efficacy of the refined extract and compositions can be evaluated by in vitro models with respect to their activities in inhibiting proliferation or differentiation, or inflammation. For example, in vitro testing can be conducted on cytokine signaling, STAT-3/STAT-1, MAPK, NFκB involved pathways.

The efficacy of the refined extract and compositions can be further evaluated by in vivo models with respect to their activities in treating diseases or disorders. For example, genetically engineered mice, including the transgenic and knockout models, can be tested.

The novel features of the application are set forth with particularity in the appended claims. A better understanding of the features and advantages of the present application will be obtained by reference to the following detailed description that sets forth illustrative embodiments, in which the principles of the application are utilized.

While preferred embodiments of the present application have been shown and described herein such embodiments are provided by way of example only. It should be understood that various alternatives to the embodiments of the application described herein may be employed in practicing the application. Those ordinary skilled in the art will appreciate that numerous variations, changes, and substitutions are possible without departing from the application. It is intended that the following claims define the scope of aspects of the application and that methods and structures within the scope of these claims and their equivalents be covered thereby.

It is to be understood that, if any prior art publication is referred to herein, such reference does not constitute an admission that the publication forms a part of the common general knowledge in the art. All documents, or portions of documents, cited in the application including, without limitation, patents, patent applications, articles, books, manuals, and treatises are hereby expressly incorporated by reference in their entirety for any purpose.

The percentage herein is expressed by weight relative to the weight of the extract or the specified product, unless otherwise specified.

Further aspects and advantages of the invention will be disclosed in the following illustrative experimental section.

EXAMPLES

1. Preparation of Refined Indigo Naturalis Extracts and Analytical Methods for Analysis Example 1

Preparation of a Refined Indigo Naturalis Extract

Qingdai as used in the following preparation is obtained from Delong Pharmaceutical (Indigo 2.62% and Indirubin 0.284% (HPLC method depicted in Example 8A) and tryptanthrin 0.0046% (HPLC method depicted in Example 8B)).

500 g of Qingdai were suspended in 10 L ethyl acetate. The mixture was stirred in reflux for two hours, and then filtered at 75° C. The filtrate was concentrated at reduced pressure to yield a dark solid. The crude extract was stirred in 250 mL hexane and heated to reflux for one hour. After cooling to room temperature, the suspension was filtered to give a dark residue (a crude extract).

0.50 g of the dark residue were refluxed in 25 mL hexane again for one hour, and cooled to room temperature, followed by filtration to give a refined extract as a dark red solid 452 mg. HPLC: 62.9% indirubin, 12.9% indigo, and 0.53% tryptanthrin.

Example 2

Preparation of a Refined Indigo Naturalis Extract 500 g of Qingdai as used in Example 1 were suspended in 10 L alcohol (ethanol). The mixture was stirred in reflux for two hours, and then filtered at 75° C. The filtrate was concentrated at reduced pressure to yield a dark solid, which was stirred in 260 mL hexane and heated to reflux for one hour. Upon cooling to room temperature, the suspension was filtered to give a dark residue.

0.80 g of the dark residue were refluxed in 24 mL alcohol (ethanol) for an additional hour, and then cooled to room temperature, followed by filtration to give a refined extract as a dark red solid (538 mg). HPLC: 83.6% indirubin, 6.35% indigo, and 0.75% tryptanthrin.

Example 3

Preparation of a Refined Indigo Naturalis Extract 500 g of Qingdai as used in Example 1 were suspended in 10 L ethyl acetate. The mixture was stirred in reflux for two hours, and then filtered while hot. The filtrate was concentrated at reduced pressure to yield a dark solid. The crude extract was stirred in 250 mL hexane and heated to reflux for one hour. After cooling to room temperature, the suspension was filtered to give a dark residue.

0.75 g of the dark residue were refluxed in 22.5 mL ethanol for one hour, and cooled to room temperature, followed by filtration to give a refined extract as a dark red solid (538 mg). HPLC: 77.9% indirubin, 15.9% indigo, and 0.56% tryptanthrin.

Example 4

Preparation of a Refined Indigo Naturalis Extract 500 g of Qingdai as used in Example 1 were suspended in 2.1 L DMF. The mixture was stirred at 50° C. for 40 minutes. Upon cooling to 20° C., the suspension was filtered. The filtrate was concentrated at reduced pressure to yield a dark solid, which was stirred in 130 mL hexane and heated to reflux for one hour. Upon cooling to 20° C., the suspension was filtered to give a dark residue.

1.56 g of the dark residue was washed with 46.8 ml ethanol, and heated to reflux for one hour, and then cooled to 20° C., followed by filtered to yield a refined extract (766 mg). HPLC: 66.3%, indirubin, 9.76% indigo.

Example 5

Preparation of a Refined Indigo Naturalis Extract 500 g of Qingdai as used in Example 1 were suspended in 3 L DMF. The mixture was stirred at 30° C. for 1 hour, and then filtered. The filtrate was concentrated at reduced pressure to yield a dark solid, which was stirred in 230 mL hexane and heated to reflux for one hour. Upon cooling to 20° C., the suspension was filtered to give a dark residue.

1.96 g of the dark residue was washed with 59 mL 85% ethanol (85% aq. alcohol), and heated to reflux for one hour followed by filtration while hot to yield a refined extract (1.02 g). HPLC: 69.4% indirubin, 18.7% indigo, and 0.62% tryptanthrin.

Example 6

Preparation of a Refined Indigo Naturalis Extract 100 g of Qingdai was extracted with 2 L of ethanol 92% (92% aqueous ethanol) for 2 hours under reflux conditions. Upon completion, the mixture was filtered while hot on AF6 filter (Buchner) to obtain a dark blue-red solution as a filtrate. This filtrate was reduced under vacuum to dryness to give 2.4 g of dry residue. This residue was washed with 120 mL of hexane for 1 h under reflux. Upon completion, the mixture was cooled to room temperature for 2 h then filtered under vacuum to yield 312.9 mg of a dark red refined extract.

280 mg of this refined extract were washed with 15 mL of ethanol 92% (92% aqueous ethanol) for 1 h under reflux. Upon completion the solution was cooled to room temperature, and then filtered to yield 159 mg of a dark red/burgundy refined extract after drying in oven (80° C.) for 1 h30. (0.18%); HPLC: 82.31% indirubin, 8.99% indigo, and 0.81% tryptanthrin.

Example 7

Micronization Step

The micronization step of refined Indigo Naturalis extract obtained in the previous examples is performed with the following equipment:
Micronizer: spiral jet Mill Diameter 200
Feeder: this equipment is used for the dosage of powder to feed the micronizer. The dosage is made thanks to two screws. This system allows a regularity of the flow.
Micronization consists to project grains of powder with jet of air. The contact of grains permits their explosion.
Following parameters of micronization are recorded during the micronization:
Ring pressure: 6 bar
Injector pressure: 3 bar
The flow of powder feed: 25 kg/h
The micronizer allows a cylindrical enclosure—holes around the enclosure for the injection of air.
Powder is introduced in the micronizer; grains are propelled thanks to jet of air. When grains have the good size, they are concentrated in the center of the micronizer and they are breathed. To avoid any contamination by foreign particles or broken pieces of the equipment, an additional sieving (sieve: 700 μm) is performed.
The step is done manually after the micronization and before the packaging.
A granulometric analysis of the homogeneous product obtained was carried out according to the particular size distribution (PSD) method [Analytical specifications: D99≤30 μm].

Example 8

Analytical Methods for Analysis

A—Reversed Phase HPLC Method:
A new reversed phase HPLC method to quantitate indigo and indirubin simultaneously was established based on European Pharmacopoeia (Pharmeuropa Vol. 20, No. 1, January 2008, P118-119.), Chinese Pharmacopoeia (2010 Edition, P185) and literatures (Chen L W, Liao W, Yang M. Jia D Y, He P, Chen S M, Fu C M. Determination of indigo and indirubin in Indigo Naturalis by HPLC. West China Journal of Pharmaceutical Sciences, 2008, 23(6), 714-715; Liu Z Y, Su Z T, Gao Y N, Yang M. Simultaneously determination of indigo and indirubin in Indigo Naturalis by HPLC. China Pharmacist 2010, 13(3), 324-326).

The chromatographic system (Agilent 1200 series) consisted of a G1322A degasser, a G1211A pump, a G1367B autosampler, a G1316A column oven and a G1315B DAD detector. Other apparatus included a SK7200H ultrasonic device (China) and a Milli-Q water purification system (USA).

Six batches of Qingdai were collected from three vendors in China. Indigo standard was purchased from Tokyo Chemical Industry Co. (Japan, >98%). Tryptanthrin was bought from Accela Co. (China, 97%). Indirubin was synthesized and recrystallized at Hutchison Medipharma (HMP) (>99% in HPLC).

Organic filter membrane (0.45 μm, China), Dimethyl formamide (DMF, analytical grade), methanol (HPLC grade), formic acid (FA, HPLC grade), triethylamine (TEA, analytical grade) and ultra-pure water purified with Milli-Q water purification system were used in the experiments.

Pretreatment of DMF solution: 500 mL of DMF was blown with dry $N_2$ for half an hour, then 0.5 mL TEA was added and mixed to give a DMF solution (containing 0.1% TEA, free of oxygen). This DMF solution was used in sample preparation.

50 mg of Qingdai was suspended in 50 mL DMF solution. After ultrasonic extraction for 10 min, the suspension was filtered through 0.45 μm syringe filter to generate the test solution of Qingdai.

20 mg of refined extract (obtained from Example 2) was suspended in 200 mL DMF solution. After ultrasonic extraction, the suspension was filtered through a 0.45 μm syringe filter to generate the test solution of the extract.

Figure 1A:
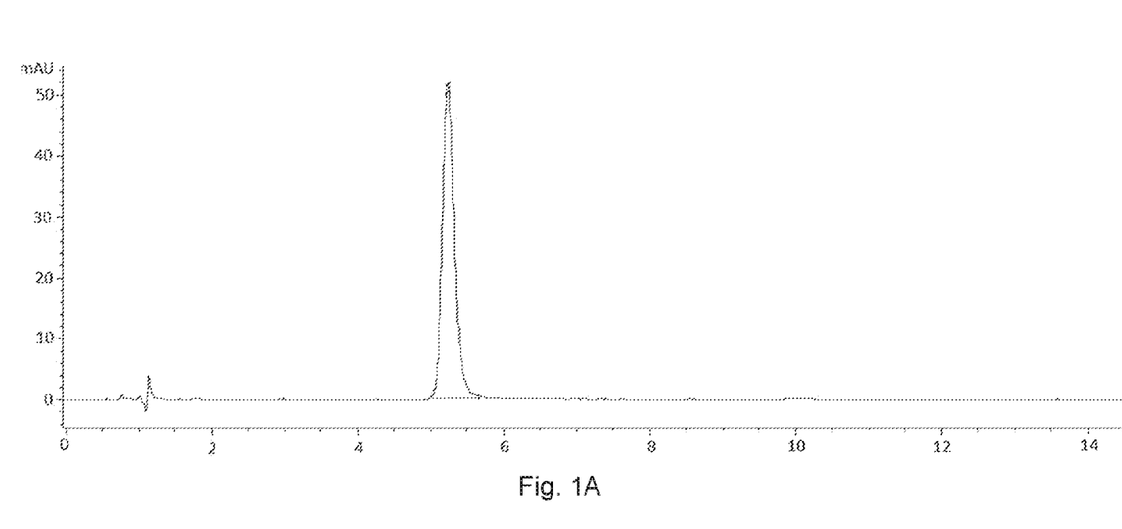
Figure 1B:
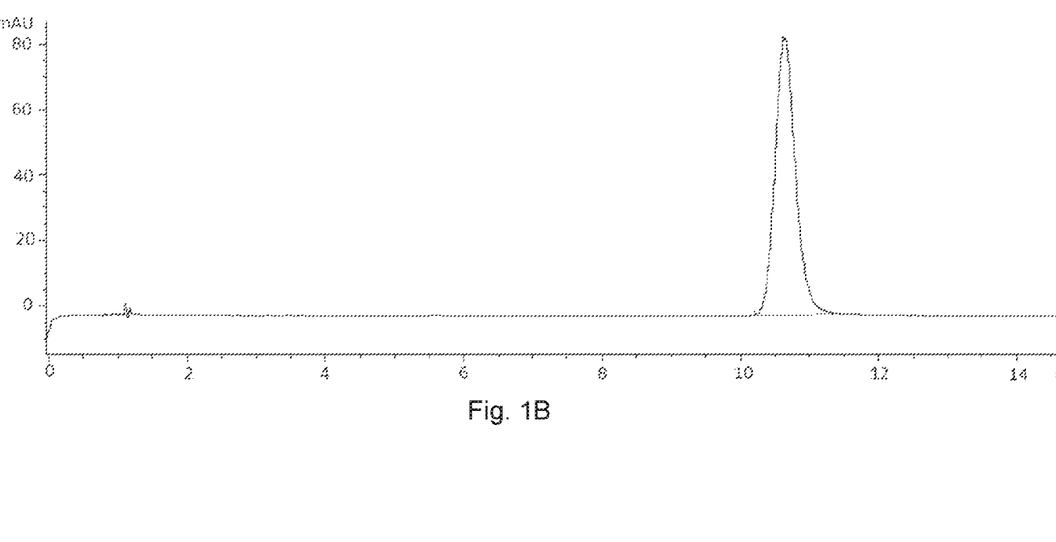

The separation was performed on a Waters Symmetry C18 column (5 μm, 3.9×150 mm). The mobile phase was 65% methanol (containing 0.05% FA). The flow rate was 1.0 mL/min for 15 min and the column temperature was 25° C. Injection volume was 4 μL. Detection wavelength was 289 nm so that indigo and indirubin could be assayed simultaneously. Indigo and indirubin could be analyzed simultaneously in one injection. Typical HPLC chromatograms of indigo and indirubin were shown in FIG. 1.

B—HPLC Analytical Method to Quantitate Tryptanthrin:
A new HPLC analytical method to quantitate tryptanthrin was also established. The sample concentration would be adjusted accordingly due to the low concentration of Tryptanthrin in both Qingdai and its enriched product, the refined extract. The analyses were performed at 25° C. on a Waters Symmetry C18 column (5 μm, 3.9×150 mm). The mobile phase was methanol (containing 0.05% FA, eluent B) and water (containing 0.05% FA, eluent A). The gradient elution profile was as follows: 50% B isocratic (12 min), 50% to 100% B (1 min), 100% B isocratic (6 min) and 100% to 50% B (1 min). The flow rate was 1.0 mL/min and the column temperature was 25° C. Injection volume was 10 μL. Detection wavelength was 254 nm.

400 mg of Qingdai was suspended in 20 mL DMF solution. After ultrasonic extraction for 20 min, the suspension was filtered through 0.45 μm syringe filter to provide the test solution of Qingdai.

15 mg of refined extract (obtained from Example 2) was suspended in 20 mL DMF solution. After ultrasonic extraction, the suspension was filtered through 0.45 μm syringe filter to provide the test solution of refined extract.

Figure 2A:
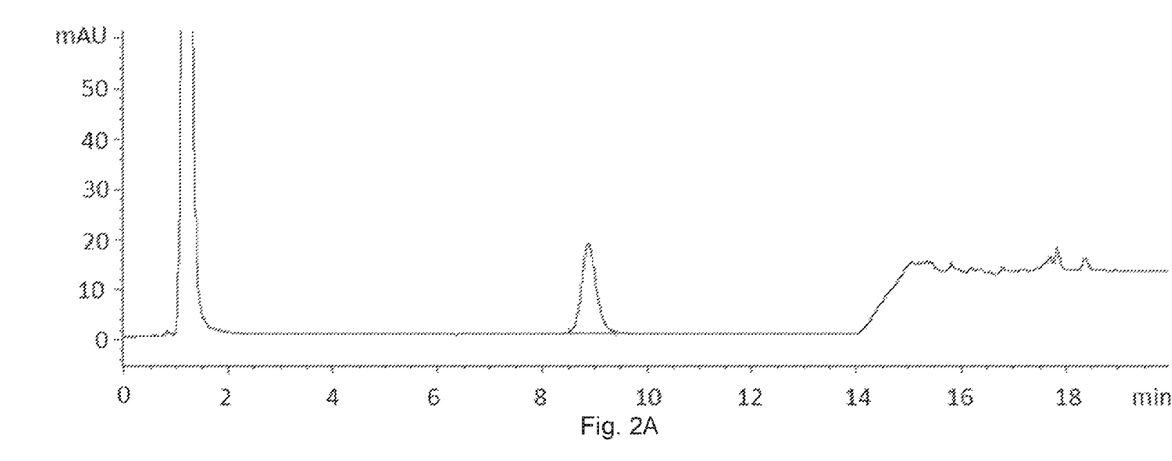
Figure 2B:
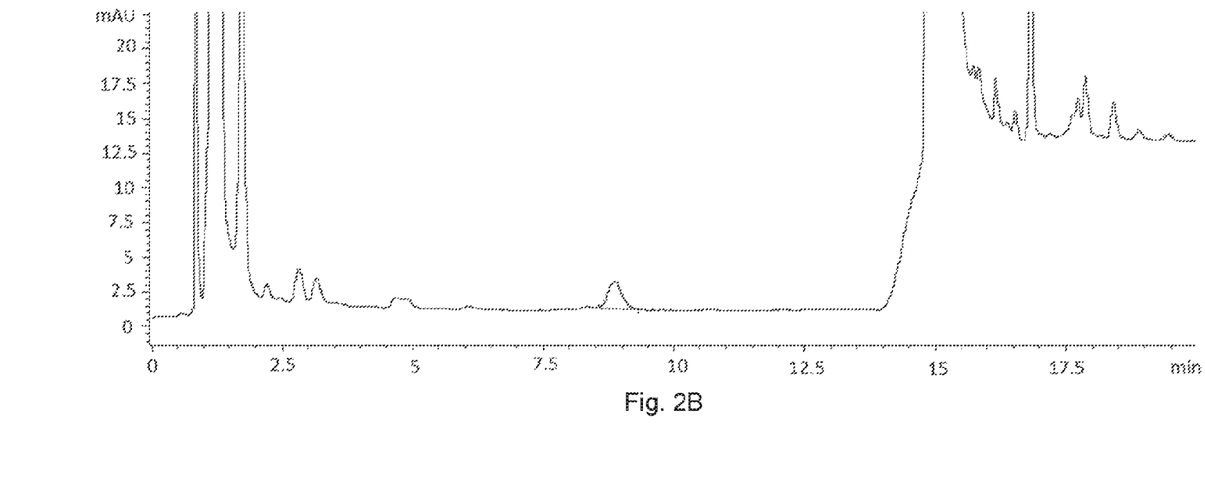
Figure 2C:
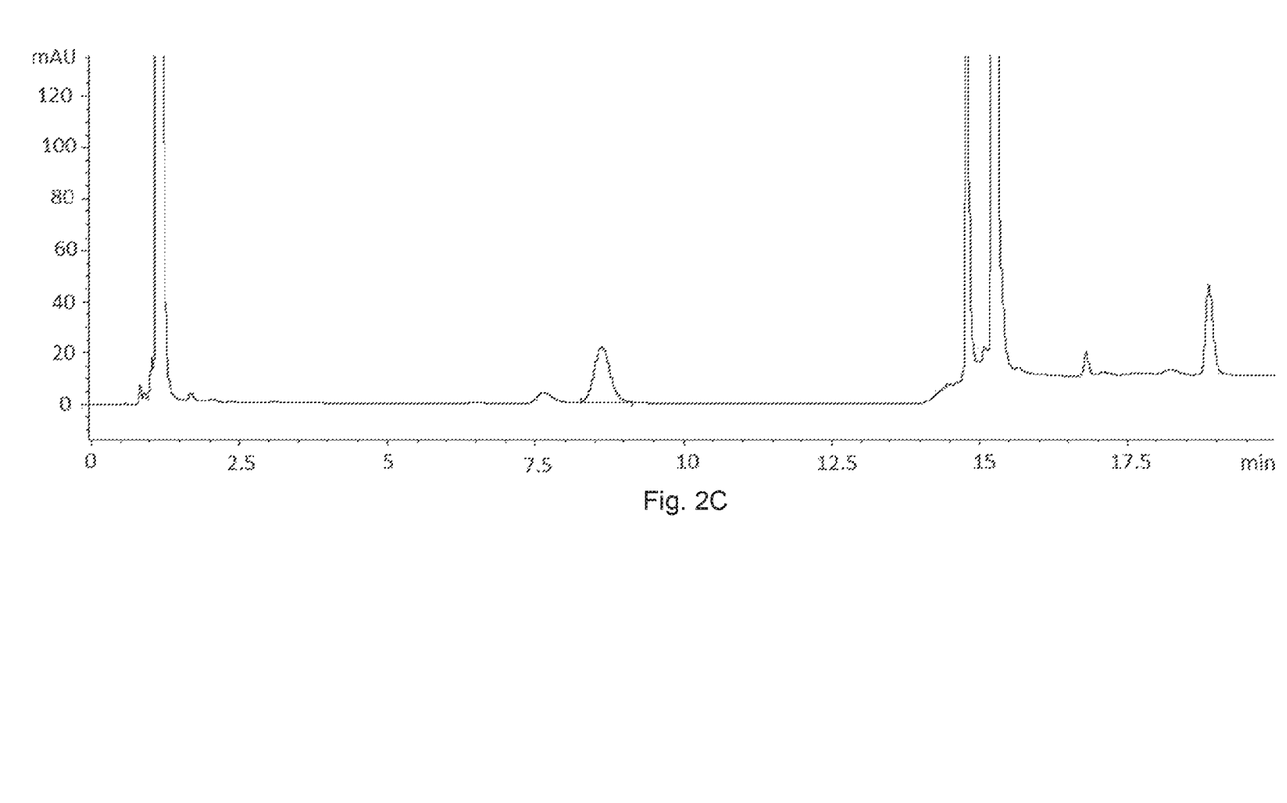

Typical HPLC chromatograms of thryptanthrin, Qingdai and a refined extract were shown in FIG. 2.

Example 9

Long Term Stability of a Refined Indigo Naturalis Extract

A refined Indigo Naturalis extract prepared according to example 6 has been submitted to stability conditions. The HPLC characterization of the prepared extract is as follows: 80.16% indirubin; 10.95% indigo; 0.64% tryptanthrin.

The storage conditions used during stability study are 25° C.±2° C. and 60% RH±5% RH in a climatic room (Piardi CC1400).

According to the GUIDELINE ON QUALITY OF HERBAL MEDICINAL PRODUCTS (CPMP/QWP/2819/00 rev 01), qualitative attributes have to comply with the limits [Limits: content of indirubin (% dried extract)=65.0-85.0; content of indigo (% dried extract)=5.0-15.0; content of tryptanthrin (% dried extract)≥5.0.

Variations in content of markers have not to exceed ±10% of the initial assay values.

Results are shown in the following table 1.

TABLE 1

| Markers | T0 Content (% dried extract) | T0 % of initial assay value | 1 month Content (% dried extract) | 1 month % of initial assay value | 3 months Content (% dried extract) | 3 months % of initial assay value | 6 months Content (% dried extract) | 6 months % of initial assay value |
|---|---|---|---|---|---|---|---|---|
| Tryptanthrin | 0.64 | 100 | 0.64 | 100 | 0.65 | 101 | 0.64 | 100 |
| Indigo | 10.95 | 100 | 11.03 | 101 | 11.10 | 101 | 11.12 | 102 |
| Indirubin | 80.16 | 100 | 79.19 | 99 | 79.52 | 99 | 80.17 | 100 |
| HPLC Fingerprint | | | Complies | | Complies | | Complies | |

HPLC fingerprint at 1 month, 2 months and 3 months complies with fingerprint chromatogram at T0. Thus, qualitative attributes comply at the limits. Variation of content of Indigo, Indirubin and Tryptanthrin do not exceed the acceptable range of ±10% of the initial assay values.

Thus, a refined Indigo Naturalis extract prepared according to the invention is stable at least 6 months at 25° C. and 60% RH.

2. In Vitro Evaluation of Refined Indigo Naturalis Extracts in Biochemical and Cellular Assays

Example 10

In Vitro Assays and Results

A. General Reagents:
DMSO, Sigma-Aldrich, St. Louis, Mo., Cat. No. D2650
Janus kinase 1 (JAK1), Life Technologies™, Cat. No. PV4774
Janus kinase 1 (JAK2), Life Technologies™, Cat. No. PV4210
Janus kinase 1 (JAK3), Life Technologies™, Cat. No. PV3855
CDK1, Life Technologies™, Cat. No. PV3292
CDK2, Life Technologies™, Cat. No. PV3267
CDK5, Life Technologies™, Cat. No. PV3000
Z'-LYTE® Kinase Assay Kit—Tyrosine 6 Peptide, Life Technologies™, Cat. No. PV4122
Z'-LYTE® Kinase Assay Kit—Ser/Thr 12 Peptide, Life Technologies™, Cat. No. PV3673
Dulbecco's modified Eagle's medium (DMEM), Life Technologies™, Cat. No. C11965
RMPI-1640, Life Technologies™, Cat. No. A10491
Fetal bovine serum (FBS), Life Technologies™, Cat. No. 10099141
EpiLife® Medium, Life Technologies™, Cat. No. M-EPI-500-CA
HKGS, Life Technologies™, Cat. No. S-001-5
Recombinant human IL-2, Peprotech Inc, Cat. No. 200-02
Recombinant human IL-6, Peprotech Inc, Cat. No. 200-06
Recombinant human IL-3, Peprotech Inc, Cat. No. 200-03
Recombinant human GM-CSF, Peprotech Inc, Cat. No. 300-03
Recombinant human IL-22, Peprotech Inc, Cat. No. 200-22
Recombinant human TNFα, R&D, Cat. No. 210-TA-010
Lipopolysaccharide (LPS), Calbiochem, Cat. No. 437650
Anti-Human CD3 Functional Grade® Purified (aCD3) (Clone: OKT3) eBioscience, Cat. No. 16-0037-85
Anti-Human CD28 Functional Grade® Purified (aCD28) (Clone: CD28.2), eBioscience, Cat. No. 16-02897-85
phospo-STAT3 (Y705) antibody (rabbit-anti-human), Cell Signaling Technology, Cat. No. 9145
phospo-STAT5 (Y694) antibody (rabbit-anti-human), Cell Signaling Technology, Cat. No. 9359
Actin antibody (mouse-anti-human) Sigma-Aldrich, Cat. No. A1978
Goat anti-rabbit IgGAlexa 488, Life Technologies™, Cat. No. A11034
Goat-anti-rabbit IROYE 800CW, Li-COR Bioscience, Cat. No. 926-32211
Goat-anti-mouse IROYE 800CW, Li-COR Bioscience, Cat. No. 926-32210
Human IFNγ ELISA Kit, R&D, Cat. No. DY285
Human TNFα ELISA Kit, R&D, Cat. No. DY210
Human IL-1β ELISA Kit, R&D, Cat. No. DY201
Human IL-6 ELISA Kit, R&D, Cat. No. DY206
Thiazolyl Blue Tetrazolium Blue (MTT), Sigma-Aldrich, Cat. No. M2128
CellTiter-Glo® Luminescent Cell Viability Assay, Promega, Cat. No. G7572
CytoTox-ONE™ Homogeneous Membrane Integrity Assay, Promega, Cat. No. G7891
Luciferase Assay, Promega, Cat. No. E4550
iBlot® Transfer Stack, Regular (Nitrocellulose), Life Technologies™, Cat. No. IB3010-01
Propidium iodide, Sigma-Aldrich, Cat. No. P4170
Ribonuclease A, Sigma-Aldrich, Cat. No. R6513
1×PBS Buffer (1 L): NaCl 8.0 g, KCl 0.2 g, $Na_2HPO_4$-$12H_2O$ 3.58 g, $KH_2PO_4$ 0.24 g, dissolved in 1 L MilliQ $ddH_2O$, pH adjusted to 7.4.
1×SDS loading buffer: 50 mM Tris-HCl/pH8.8, 2% SDS, 10% glycerol, 0.1% bromophenol blue, 100 mM DTT.

B. Cell and Cell Lines
HepG2, a human hepatocellular carcinoma cell line, purchased from Shanghai Institutes for Biological Sciences (SIBS) (Shanghai, China, Cat. No. TCHu 72), were cultured in DMEM containing 10% FBS.

TF1, a human erythroleukemia cell line, purchased from American Tissue Culture Collection (ATCC) (Manassas, Va., Cat. No. CRL-2003™), were cultured in RMPI-1640 containing 10% FBS and 2 ng/mL of GM-CSF at 37° C. with 5% $CO_2$.

PBMCs: Normal human blood samples from healthy adult donors were collected in heparinized tubes. Each independent experiment used blood from a single healthy donor. Mononuclear cells (PBMCs) were isolated using Ficoll-Paque Plus reagent (Amersham Pharmacia Biotech, Sweden, Cat. No. 17-1440-02) according to protocol recommended by the manufacturer and cultured in RMPI-1640 containing 10% FBS at 37° C. with 5% $CO_2$.

Primary T cells: Mononuclear cells (PBMC) were isolated using Ficoll-Paque Plus reagent (Amersham Pharmacia Biotech, Sweden, Cat. No. 17-1440-02) according to protocol recommended by the manufacturer. Then cells were activated by using anti-CD3 (1 μg/mL) and anti-CD28 (5 μg/mL) for 3 days, and expanded in RMPI-1640 containing 10% FBS and long/mL IL-2 at 37° C. with 5% $CO_2$ every 2-3 days for 2 weeks prior to performing experiments.

HaCaT, a human epidermal keratinocyte line from The Second Military Medical University (SMMU), China, was cultured in DMEM containing 10% FBS.

HEKa, human epidermal keratinocytes isolated from adult skin, purchased from Life Technologies™ (Carlsbad, Calif., USA, Cat. No. C-005-5C) and cultured in EpiLife 0 Medium containing HKGS at 37° C. with 5% $CO_2$.

293/NFkB-Luc cell line was purchased from Panomics (Fremont, Calif., Cat. No. RC0014). It was obtained by co-transfection with pNFκB-Luc and pHyg into a human embryonic kidney 293 cells, followed by hygromycin selection. The cells were cultured in DMEM containing 10% FBS and 100 μg/mL hygromycin B (Life Technologies™, Cat. No. 10687-010).

C. Kinase Assay

JAK1/2/3 kinase assays were performed in vitro using recombinant human JAK1/2/3 and Z'-LYTE® Kinase Assay Kit—Tyrosine 6 Peptide. CDK1/2/5 kinase assays were performed in vitro using recombinant human CDK1/2/5 and Z'-LYTE® Kinase Assay Kit—Ser/Thr 12 Peptide. All reactions (20 μL) were started by adding 2.5 μL of positive control (CP-690550 for JAK kinase assay and Staurosporine for CDK kinase assay) or the test articles (i.e., samples) in 4% DMSO solution, 5 μL of Kinase/Peptide substrate Mixture or Phospho-Peptide solution, 2.5 μL ATP Solution (100 μM) or 1.33× Kinase Buffer. The 384-well assay plate (Corning, Cat. No. 3575) was mixed and incubated at room temperature for 1 hour. 5 μL of the Development Solution was then added to each well, mixed and incubated at room temperature for another 1 hour. The kinase reactions were then stopped by adding 5 μL of the Stop Reagent followed by recording 450 nm and 520 nm fluorescence's using Perkin-Elmer Victor III (Perkin-Elmer Life Sciences, Boston, Mass.) plate reader.

D. Acumen Assay

For IL-6 induced STAT3 phosphorylation, HepG2 were seeded in 96 well plates at $5.4 \times 10^3$ cells per well in serum-free DMEM media at 37° C., 5% $CO_2$ overnight. After incubation with CP-690550 or test articles for 30 minutes, cells were stimulated by adding 100 ng/mL human recombinant IL-6 (1:10) to each well for 15 minutes.

For IL-3 induced STAT5 phosphorylation, TF-1 was seeded in 96-well plates at $1 \times 10^4$ cells per well at 37° C., 5% $CO_2$ for 3 hours. After incubation with CP-690550 or test articles for 30 minutes, cells were stimulated by adding 100 ng/mL human recombinant IL-3 (1:10) to each well for 30 minutes.

HepG2 or TF1 cells were then fixed in 2% paraformaldehyde for 45 minutes at room temperature and incubated in ice-cold methanol for 30 minutes. After washing with PBS, cells were incubated with anti-phospho-STAT3 (Y705) or anti-phospho-STAT5 (Y694) antibody respectively at 4° C. overnight. Goat anti-rabbit IgG Alexa 488 secondary antibody was added for 90 minutes prior to PBS washes. Cells were counted following incubation in PBS containing 7.5 μM Propidium iodide and 100 μg/mL Ribonuclease A for 60 minutes in the dark. Plate was read on an Acumen X3 instrument (TPP Labtech, Hertfordshire SGB, UK).

E. Western Blots

HEKa were seeded in 6-well plates at $2 \times 10^5$ cells/well at 37° C., 5% $CO_2$ overnight. After incubation with test article for 30 minutes, the cells were stimulated with 100 ng/mL IL-22 for 30 minutes.

After the treatment, samples were collected in 1×SDS loading buffer. Protein samples were boiled for 15 minutes and collected by centrifugation at 14,000 g for 10 min at 4° C. The supernatants were used or immediately stored at −80° C. For Western blot analysis, samples were separated on a 10% Tris-HCL gradient electrophoresis gel (Bio-Rad Laboratories). Gels were blotted onto a iBlot® Transfer Stack, Regular (Nitrocellulose) which was blocked in 5% nonfat dry milk and probed using anti-phospho-STAT3 (Y705) antibody or anti-Actin antibody at 4° C. overnight, respectively. The membrane was then incubated with appropriate IDRye 800CW secondary antibody followed by detection using Odyssey infrared imaging System (Li-COR Bioscience, Lincoln, Nebr., USA).

F. Reporter Assays

For reporter gene assays, the 293/NFκB-Luc was seeded in 96-well plate at $4 \times 10^4$ cells per well overnight. After the incubation with Andrographolide (LGT) or test articles for 30 minutes, cells were stimulated by adding 100 ng/mL TNFα (1:10) to each well for 6 hours. Cell lysates were prepared by removing media and adding lysis buffer. 5× volume Luciferase Assay Reagent was added to each well prior to read plate. Luminescence was recorded using Perkin-Elmer Victor III plate reader (Perkin-ElmerLife Sciences, Boston, Mass., USA).

G. ELISA Assay

Primary T cells were seeded in 96-well plates at $8 \times 10^4$ cells/well. Test articles were added into the cultures and incubated at 37° C., 5% $CO_2$. After 30 minutes, the cell suspension in each well was transferred to another 96-well plate coated with a CD3 (1 μg/mL) and a CD28 (5 μg/mL) and incubated at 37° C. with 5% $CO_2$ for 22 hours. The media were removed and stored at −80° C. until assayed. IFNγ concentrations were determined using a commercial ELISA kit (R & D Systems), following the manufacturer's instruction.

PBMCs were seeded in 96-well plates at $3 \times 10^4$ cells per well. Test articles were then added into the culture and incubated at 37° C., 5% $CO_2$. After 30 minutes, 1 μg/mL LPS (1:10) was added to the culture. For quantitation of protein levels, the plates were incubated for 18 hours. The media were removed and stored at −80° C. until assayed. TNFα, IL-1β and IL-6 concentrations were determined using commercial ELISA kits (R & D Systems), following the manufacturer's instructions.

H. MTT Assay

HaCaT were seeded in 96-well plates at $4\times10^4$ cells/well overnight. Stausporine or test articles were then added into the culture and incubated at 37° C., 5% $CO_2$ for 72 hours. After removal of the media, the cells in 96-well plates were exposed to 100 μL of MTT (0.5 mg/mL in DMEM containing 10% FBS per well and incubated for 3 hours at 37° C., 5% $CO_2$. Subsequently, the supernatants were removed and 150 μL of DMSO were added to each well. The plate was incubated in the dark for 10 minutes and the absorbance at 492 nm was recorded immediately using Multiskan MK3microplate reader (Thermo Life Sciences, HK, China).

I. Cell Viability Assay

CellTiter-Glo® Luminescent Cell Viability Assay Kit was used to investigate cell viability. HEKa were seeded in 96-well opaque-walled plate at $1\times10^4$ cells/well overnight. Dithranol or test articles were then added into the culture and incubated at 37° C., 5% $CO_2$ for 48 hours. Cells were lysed with CellTiter-Glo® Reagent equal to the volume of cell culture media present in each well, and contents mixed for 2 minutes to induce cell lysis. Plate was incubated at room temperature for 10 minutes to stabilize luminescent signal. Luminescence was recorded using Perkin-ElmerVictor III plate reader (Perkin-Elmer Life Sciences, Boston, Mass., USA).

J. LDH Release Assay

Lactate dehydrogenase (LDH) release assay kit was used to investigate cytotoxicity. HEKa were seeded in 96-well opaque-walled plates at $4\times10^4$ cells/well overnight. Dithranol or test articles were then added into the culture and incubated at 37° C. under 5% $CO_2$ for 24 hours. Supernatants and cell lysates were prepared. 1× volume of CytoTox-ONE™ Reagent equal to the volume of supernatants or cell lysates were added to each well followed by mixing for 30 seconds and incubating at 25° C. for 10 minutes. Stop solution equal to 50% volume of the supernatants or cell lysates were added to each well to stop the reaction, and fluorescence with an excitation wavelength of 560 nm and an emission wavelength of 590 nm were recorded using SpectraMax M2 (Molecular Devices, Sunnyvale, Calif., USA).

K. TNFα-Induced NFκB Activation

Pro-inflammatory cytokines and chemokines play important roles in pathogenesis of psoriasis. NFκB is clearly one of the most important regulators of pro-inflammatory cytokine and chemokine gene expression. Therefore, inhibitory potency of Qing Dai and its refined extracts on TNFα-dependent NFκB activation was investigated in HEK 293/NFκB-Luc. As shown in Table 1, TNFα stimulated NFκB-dependent luciferase expression and pretreating cells with Tripterygium Glycoside blocked NFκB activation in a concentration dependent manner. Indigo Naturalis refined extract had microgram/g activities on TNFα-dependent NFκB activation on the experimental condition. (see Table 1).

L. $IC_{50}$ Determinations

All IC50 values were determined by using Xlfit™ software (version 2.0) from ID Business Solutions (Guildford, UK). Background was defined in culture with cells treated with DMSO only and was subtracted for $IC_{50}$ calculations.

M. Results

Some in vitro assay results of Indigo Naturalis refined extracts are shown in Table 2 below, wherein Indigo Naturalis A is obtained from Delong Pharmaceutical: (Indigo 2.62%, Indirubin 0.284%; Tryptanthrin 0.0046%).

TABLE 2

| Sample | pro-inflammatory cytokine production $IC_{50}$ (NFκB) μg/mL | HaCaT proliferation $IC_{50}$ μg/mL | HEKa Viability $IC_{50}$ μg/mL |
|---|---|---|---|
| Staurosporine | | 3.18 (nM) +/− 2.19 | |
| LGT | 0.00045 | | |
| Indigo Naturalis A** | | 2.42/2.43 | |
| Example 4 | 10.87/63.53/ 10.37/25.75 | 1.57/<0.82/1.02 | |
| Example 1 | 8.47/15.40 | | 2.91 ± 0.49 (n = 2) |
| Example 3 | 37.23/>100 | | 1.71 ± 0.54 (n = 3) |
| Example 2 | 51.03/41.79 | | 1.75 ± 0.48 (n = 4) |
| Example 5 | 24.66/32.97 | | 2.21 ± 0.45 (n = 4) |

**Indigo Naturalis A: Indigo Naturalis from Delong Pharmaceutical: Indigo 2.62%, Indirubin 0.284%; Tryptanthrin 0.0046%

3. In Vivo Evaluation of Refined Indigo Naturalis Extracts in Animal Models

Example 11

In Vivo Assays and Results

A. Materials and Methods

Animals

BABL/c mice, male, body weight 19-22 g, purchased from Shanghai SLC AnimalCenter.

Room temperature: 24±1° C.

Room relative humidity: 40-70%

Light cycle: Fluorescent light for 12-hour light (8:00-20:00) 12-hour dark

Animal hosting: 4 mice/cage

Food: Free access to food (irradiated, Shanghai SLAC Laboratory Animal Co. Ltd., China)

Water: Free access to tap water from local supply (first filtered by Molanimal ultrapure water machine from the municipal water supply)

Instruments

MJ Research PTC-200 Peltier Thermal cycler (Alpha Unit™ Block Assembly for PTC DNA Engine™ systems)

Applied Biosystems 7500 realtime PCR system

Digimatic micrometer caliper: Mitutoyo, Japan. Accuracy: 0.001 mm

Reagents

Recombinant mouse IL-22 (rmIL-22), Novoprotein (sinobio), Cat. C047, Lot. 0375351

High capacity cDNA Reverse Transcription kit, Applied Biosystems, Part No.: 4368813, Lot: 0909069

Thermo Scientific ABsolute SYBR Green Rox Mix, Thermo Scientific, Cat: AB-1163/A, Lot: 0911/16

Positive Control

Protopic® (tacrolimus, FK506), 0.1% ointment, Astellas Toyama Co., Ltd. Toyama Plant, H20100079, Lot: 028680.

Dosing Regimen

Different concentrations of test samples, vehicle, or 0.1% of FK506 ointment, were topically administrated at 1% one hour after the induction of model and then given daily from day 1 to day 11, twice a day. The first day of administration of a test article was regarded as day 0.

Route of Administration

Topical application, b.i.d.

Establishment of IL-22 Induced Psoriasis-Like Mouse Models

Intradermal injection of 20 μL PBS, either alone or containing 100 or 500 ng recombinant mouse IL-22 (eBiosience), was administered into the ears of anesthetized mice using a 30-gauge needle every other day for eleven days. Ear thicknesses were measured before injection on day 0 and thereafter on days without injections. Ear measurements were taken at the center of the ears using a digimatic micrometer caliper (Mitutoyo).

Twenty-four hours after the last IL-22 treatment, mice were sacrificed, and ears were collected for further analysis.

Histological Examination

Ears were collected at necropsy, fixed in 10% buffered formalin phosphate, embedded in paraffin, sectioned, and stained with hematoxylin/eosin (H&E). Microscopic sections were graded by the number and severity of lesions.

Statistical Methods

Results of ear thickness data were expressed as mean±S.E.M. AUC of ear swelling was calculated by the ear thickness data from day 0 to day 11, and analyzed by repeated-measured ANOVA methods with JMP® software. Cytokine protein and gene expression data were evaluated with a one-way ANOVA and followed by student's t-test for post-hoc analysis. (Significance level was set at $p<0.05$).

Group and Dosing

Figure 3:
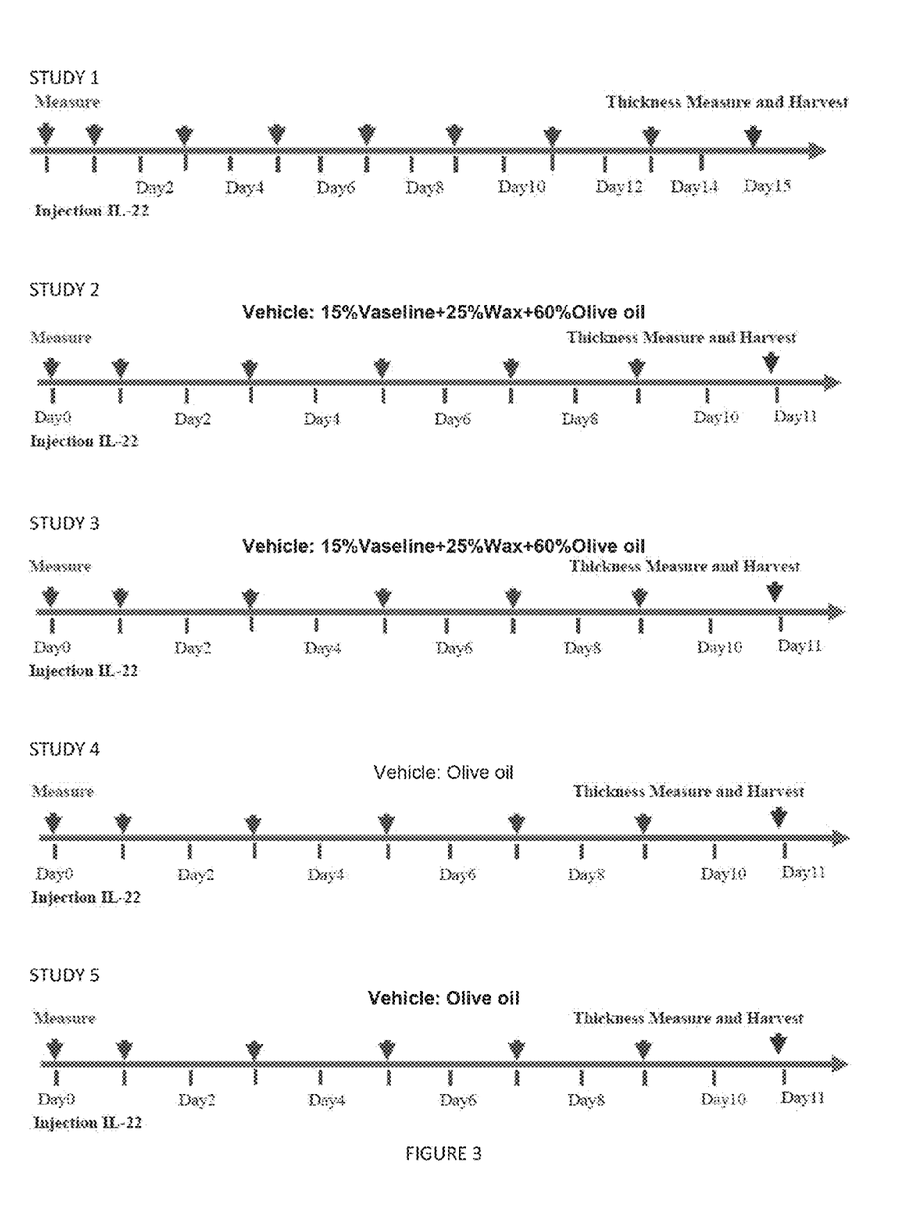
FIG. 3: Group and dosing for in vivo evaluation of extracts from Qingdai in IL-22 induced psoriasis model. Five studies were designed and outlined in study 1-5, respectively. In Study 1, 100 ng and 500 ng of IL-22 in 200 μL saline, i.d., were used for induction. In study 2-5, 500 ng of IL-22 in 20 μL saline, i.d., were used for induction.

See FIG. 3.

Results

Some in vivo assay results of some of Indigo Naturalis refined extracts are shown in Table 3.

The invention claimed is:

1. A process of preparing an extract product from Indigo Naturalis or a plant containing thereof, comprising:
    a) extracting the Indigo Naturalis or the plant with a solvent to obtain a mixture of extraction, wherein the solvent is selected from the group consisting of dimethylformamide, ethyl acetate, ethanol, dimethylsulfoxide, dichloromethane, tetrahydrofuran, dimethylacetamide, acetone, 2-butanone, acetonitrile, isopropyl acetate, 2-methyl tetrahydrofuran, methyl tert-butyl ether, methanol, chloroform, terpene, water and a combination thereof,
    b) filtering the mixture of extraction to obtain a filtrate,
    c) concentrating the filtrate to obtain a crude extract,
    d) mixing the crude extract with hexane or heptane at a temperature not less than 50° C. to obtain a washing mixture, and
    e) filtering the washing mixture to obtain the extract product.

2. The process of claim 1, wherein the solvent used in a) is selected from the group consisting of dimethylformamide, ethyl acetate, ethanol, and a combination thereof, or an aqueous solution thereof.

3. The process of claim 2, wherein in e), the washing mixture is cooled and filtered at room temperature to obtain the extract product.

4. A process of preparing an extract product of Indigo Naturalis, comprising:
    a) extracting the Indigo Naturalis with a solvent to obtain a mixture of extraction, wherein the solvent is selected from the group consisting of dimethylformamide, ethyl acetate, ethanol, dim ethyl sulfoxi de, dichloromethane, tetrahydrofuran, dim ethyl acetami de, acetone, 2-bu-

TABLE 3

Figure 4:
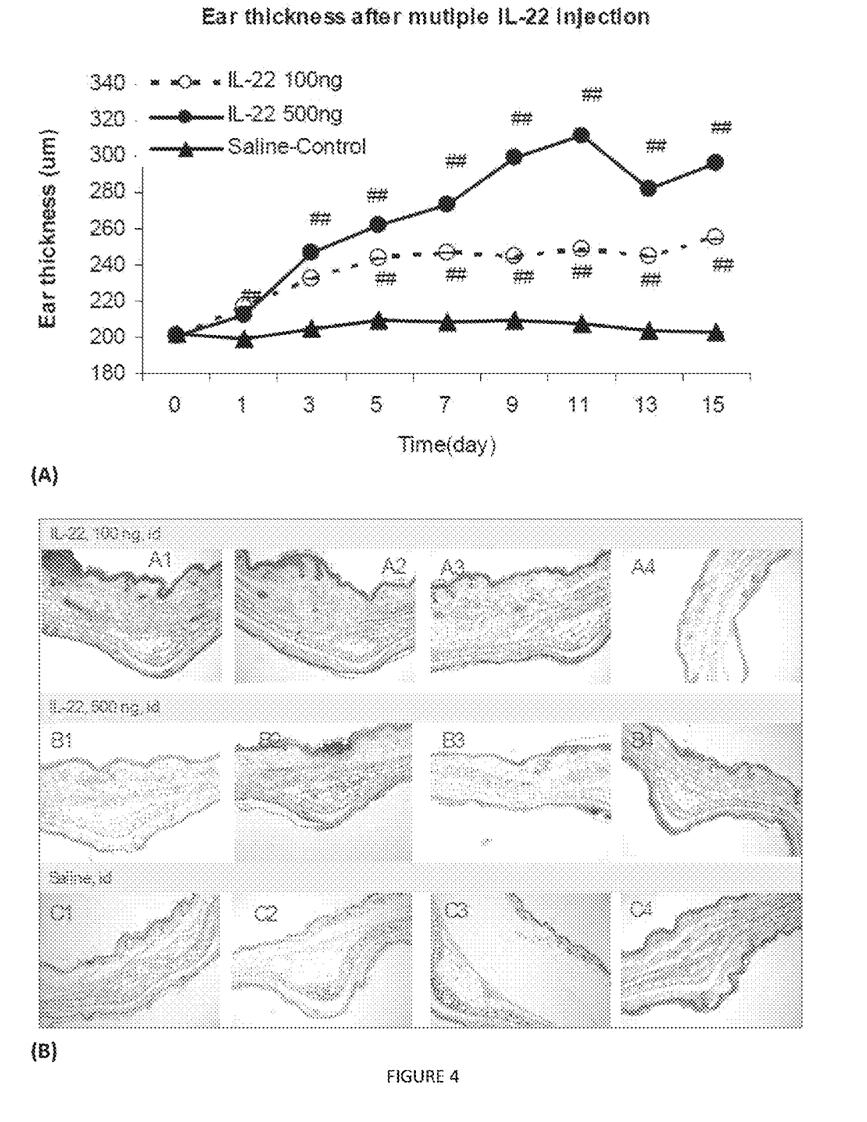
FIG. 4: Figures illustrate ear inflammation after intradermal injection of IL-22. In the studies, ears of mice were injected intradermally and ear thickness was measured on days between injections.
Figure 5:
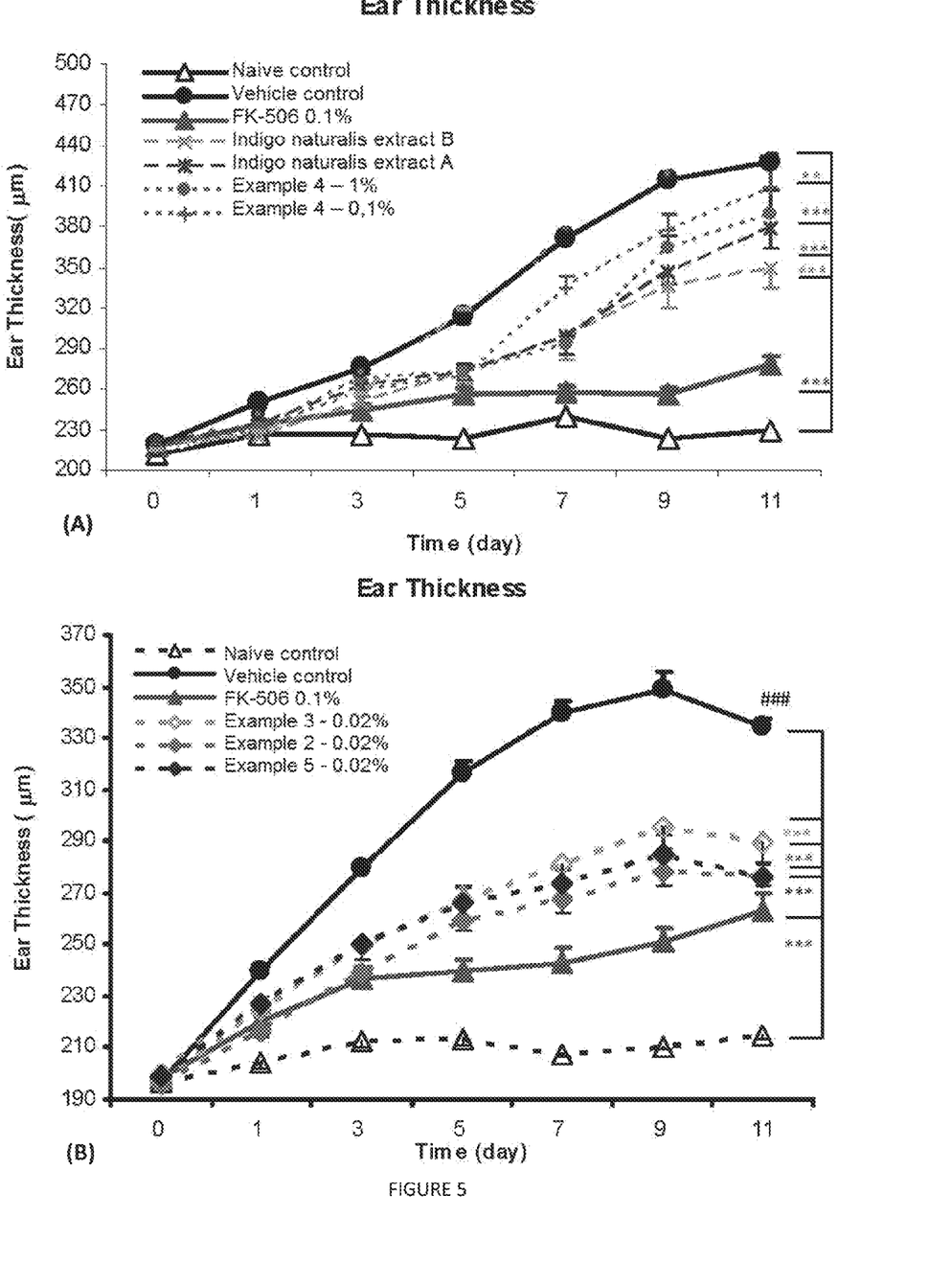
FIG. 5: Figures illustrate the effects of extracts from Qingdai on ear inflammation after intradermal injection of IL-22.

| In vivo studies | group | ear thickness on day 11 (μm) | AUC of ear thickness | inhibition of AUC of ear thickness (%) |
|---|---|---|---|---|
| study 1 (cf FIG. 4) | saline-control (naive) | 207.8 ± 1.8, 202.8 ± 2.2 (d15) | 61 | |
| | IL-22, 100 ng | 248.3 ± 1.9, 255.3 ± 15.1 (d15) | 590 | |
| | IL-22, 500 ng | 311.3 ± 18.0, 296.3 ± 5.0 | 1055 | |
| study 2 | naive control | 236.7 ± 2.8 | 172 | |
| | vehicle 1 control | 371.3 ± 8.7 | 1281 | |
| | FK506 (0.1%) | 256.8 ± 3.5 | 403 | 79.2 |
| | Indigo Naturalis B* (10%) | 328.8 ± 16.8 | 749 | 48 |
| study 3 (cf FIG. 5(A)) | naive control | 230.2 ± 4.4 | 165 | |
| | vehicle control | 428.3 ± 6.6 | 1256 | |
| | FK506 (0.1%) | 278.8 ± 5.0 | 369 | 81.3 |
| | Indigo Naturalis B* (10%) | 349.3 ± 14.6 | 703 | 50.7 |
| | Example 4 (1%) | 289.3 ± 17.4 | 876 | 34.8 |
| | Example 4 (0.1%) | 408.7 ± 18.0 | 975 | 25.7 |
| study 4 | naive control | 233.1 ± 3.6 | 238 | |
| | vehicle control | 356.4 ± 11.8 | 1301 | |
| | FK506 (0.1%) | 260.4 ± 4.5 | 446 | 80.4 |
| | Example 4 (0.5%) | 310.4 ± 4.4 | 969 | 31.3 |
| | Example 4 (0.1%) | 303.8 ± 4.3 | 868 | 40.7 |
| | Example 4 (0.02%) | 302.8 ± 6.4 | 922 | 35.7 |
| study 5 (cf FIG. 5(B)) | naive control | 214.5 ± 1.1 | 143 | |
| | vehicle control | 334.3 ± 3.3 | 1194 | |
| | FK506 (0.1%) | 263.4 ± 6.3 | 454 | 70.4 |
| | Example 3 (0.02%) | 289.6 ± 8.0 | 751 | 42.2 |
| | Example 2 (0.02%) | 276.3 ± 3.2 | 627 | 53.9 |
| | Example 5 (0.02%) | 275.5 ± 5.9 | 677 | 49.2 |

*Indigo Naturalis B: Indigo Naturalis from Qingfeng Pharmaceutical: Indigo 2.02%, Indirubin 0.216%; Tryptanthrin 0.0032% tanone, acetonitrile, isopropyl acetate, 2-methyl tetrahydrofuran, methyl tert-butyl ether, methanol, chloroform, terpene, water and a combination thereof, b) filtering the mixture of extraction to obtain a filtrate, c) concentrating the filtrate to obtain a crude extract, d) mixing the crude extract and hexane or heptane in reflux to obtain a first washing mixture, e) cooling and filtering the first washing mixture at room temperature obtain a first extract product, and f) washing the first extract product with a washing method comprising:

i. mixing the first extract product and a solvent selected from the group consisting of hexane, ethanol and an aqueous solution of ethanol in reflux to obtain a second washing mixture, and    ii. cooling and filtering the second washing mixture at room temperature to obtain a second extract product.

5. The process of claim 4, wherein in a), the solvent is selected from the group consisting of dimethylformamide, ethyl acetate, ethanol, and a combination thereof, or an aqueous solution thereof.

6. The process of claim 5, wherein in a), the solvent is ethyl acetate, ethanol or an aqueous solution of ethanol, and the mixture of extraction is obtained by mixing the Indigo Naturalis and the solvent in reflux.

7. The process of claim 6, wherein in b), the mixture of extraction is filtered at a temperature not less than 65° C. to obtain the filtrate.

8. The process of claim 7, wherein prior to d), the crude extract is added with water and filtered to remove the solvent in the crude extract.

9. The process of claim 8, wherein in d), the crude extract is mixed with hexane in reflux to obtain the first washing mixture.

10. The process of claim 9, wherein the first extract product is rinsed with ethanol and water prior to f).

11. A process of preparing a refined extract comprising at least 55% (w/w) indirubin relative to the total weight of the refined extract, the process comprising:

a) extracting the Indigo Naturalis with a solvent to obtain a mixture of extraction, wherein the solvent is selected from the group consisting of ethyl acetate, ethanol, an aqueous solution of ethanol, and a combination thereof, and the mixture of extraction is obtained by mixing the Indigo Naturalis and the solvent in reflux, b) filtering the mixture of extraction at a temperature of not less than 65° C. to obtain a filtrate, c) concentrating the filtrate to obtain a crude extract, d) mixing the crude extract and hexane in reflux to obtain a first washing mixture, e) cooling and filtering the first washing mixture at room temperature to obtain a first extract product, and f) washing the first extract product with a washing method comprising:

a) mixing the first extract product and a solvent selected from the group consisting of hexane, ethanol and an aqueous solution of ethanol in reflux to obtain a second washing mixture,    b) cooling and filtering the second washing mixture at room temperature to obtain a second extract product, and    c) drying the second extract product at a temperature of less than 80° C. to obtain a dried extract product, g) optionally washing the dried extract product with the washing method of f) one or more times to thereby obtain the refined extract.

12. The process of claim 11, further comprising micronizing the fine extract.

\* \* \* \* \*